United States Patent [19]

Wallace

[11] 4,177,033
[45] Dec. 4, 1979

[54] FLAME DETECTION ARRANGEMENTS AND THE LIKE

[75] Inventor: Malcolm R. Wallace, Fareham, England

[73] Assignee: Plessey Handel und Investments AG, Zug, Switzerland

[21] Appl. No.: 853,873

[22] Filed: Nov. 22, 1977

[30] Foreign Application Priority Data

Nov. 25, 1976 [GB] United Kingdom ............ 49219/76

[51] Int. Cl.² ............................................. F23H 5/08
[52] U.S. Cl. ........................................ 431/78; 328/6; 340/579; 431/266
[58] Field of Search ............ 340/228 R, 579; 431/78, 431/80, 25, 264, 265, 266; 328/6

[56] References Cited

U.S. PATENT DOCUMENTS

| | | | |
|---|---|---|---|
| 2,112,736 | 3/1938 | Cockrell | 340/579 X |
| 3,740,574 | 6/1973 | Taylor | 340/579 X |
| 3,836,857 | 9/1974 | Ikegami et al. | 340/579 X |
| 4,088,984 | 5/1978 | Muramoto et al. | 431/78 X |

Primary Examiner—Edward G. Favors
Attorney, Agent, or Firm—Fleit & Jacobson

[57] ABSTRACT

A circuit arrangement for utilizing the "flame (or hot gas) rectification" effect in an air gap is provided in which the air gap is defined between electrodes one of which is connected to a source of A.C. and the other of which is connected to earth or other suitable potential. A non-linear resistance device is connected in series with the air gap and a voltage sensing is provided for detecting a voltage across the non-linear resistance device, the arrangement being such that when no flame or hot gas is present in the air gap the air gap and the non-linear resistance device are virtually open-circuited so that the A.C's alternated by filter means to zero volts D.C. with a small ripple, superimposed thereon at the input to the voltage sensing circuit, whereas when flame or hot gas is present in said air gap the non-linear resistance produces a negatively predominant signal which after filtering provides a negative D.C. voltage shift with a small percentage A.C. ripple superimposed at the input to the voltage sensing circuit.

8 Claims, 10 Drawing Figures

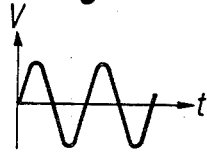
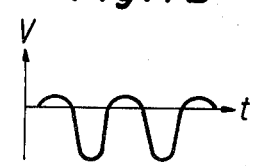
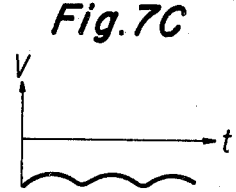
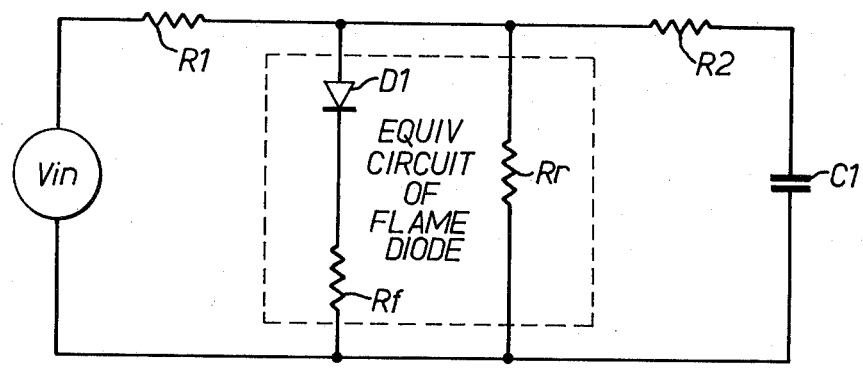
FIG. 3.
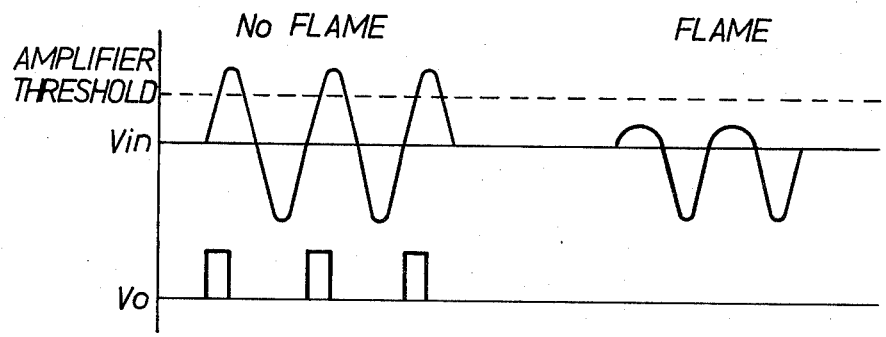
Fig. 8.
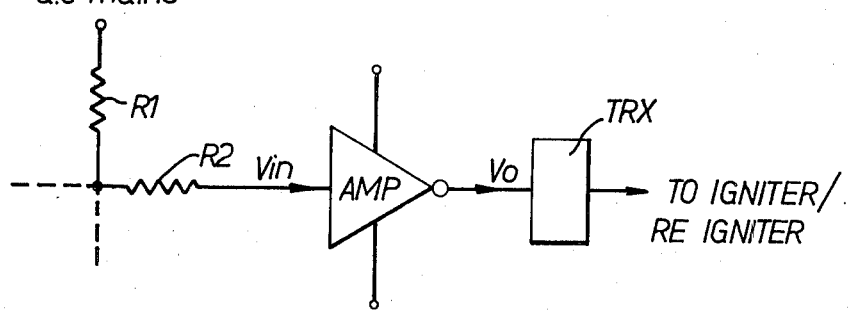
FIG. 4.

FLAME DETECTION ARRANGEMENTS AND THE LIKE

This invention relates to circuit arrangements suitable for detecting flame or high temperature gas and has application to flame detection in the burner systems of gas cookers and in furnace control and "hot" gas flow detector systems, to mention a few applications.

It is very well-known to detect the presence of a flame at a fuel burner by the utilisation of the "flame conduction" effect but this technique has been superceded by flame detection arrangements which utilise the "flame rectification" effect. Flame detection by the utilisation of the "flame rectification" effect has the following advantages over arrangements utilising flame conduction.

(1) "Flame rectification" effect arrangements can tolerate a much lower leakage resistance across a spark gap of an associated ignition circuit without false operation since an asymmetric waveform produced across the gap is more easily distinguished than pure resistance.

(2) With "Flame rectification" effect arrangements a low resistance across the spark gap, such as due to condensation, simulates the absence of flame and therefore ignition would not be inhibited as with "flame conduction" effect arrangements.

Hitherto, "flame rectification" effect arrangements have used a mains isolating transformer for applying an a.c. signal to a flame sensing probe provided in addition to the usual spark electrodes and positioned where it will be enveloped by flame. When flame is present a resulting restified signal will be produced which is filtered giving a d.c. voltage level shift which can be detected.

According to the present invention there is provided a circuit arrangement for utilising the "flame (or hot gas) rectification" effect in an air gap in which said air gap is defined between electrodes one of which is connected to a source of a.c. and the other of which is connected to a suitable potential, in which a non-linear resistance device is connected across said air gap and voltage sensing means is provided for detecting a voltage across the non-linear device. The arrangement is such that when no flame or hot gas is present in said air gap, the air gap and the non-linear resistance device are virtually open-circuited and the a.c. may be attenuated by filter means to zero volts d.c. with a small ripple superimposed thereon at the input to the voltage sensing circuit, whereas when flame or hot gas is present in said air gap the resultant rectification effect produces a negatively predominant signal across the non-linear resistance which after filtering by said filter means provides a negative d.c. votage shift with a small percentage a.c. ripple superimposed at the input to the voltage sensing circuit.

In carrying out the present invention the voltage sensing means may comprise a high impedance amplifier or a neon device.

Especially envisaged is the use of the circuit arrangement according to the invention in the detection of flame at the burner of a gas appliance (e.g. gas cooker) in which the secondary winding of a spark generating transformer is connected to the air gap so that when the voltage across the non-linear resistance device indicates the absence of flame in said air gap the voltage sensing means produces an output effective to trigger igniter/re-igniter means for pulsing said transformer and thereby cause sparking across said air gap for the ignition or re-ignition of gas.

The secondary winding of the spark generating transformer may be connected in series with the non-linear resistance device across the air gap.

By way of example the present invention will now be described with reference to the accompanying drawings in which:

FIG. 3 shows an equivalent circuit for the flame detection arrangement of FIGS. 1 and 2 when burner flame is detected;

FIG. 4 shows an alternative arrangement to FIG. 2 in which the filter capacitor is omitted;

FIGS. 7A-7C are waveforms used in explaining the circuit arrangement of FIG. 1.

FIG. 8 is a waveform used in explaining the circuit arrangement of FIG. 4.

Figure 1:
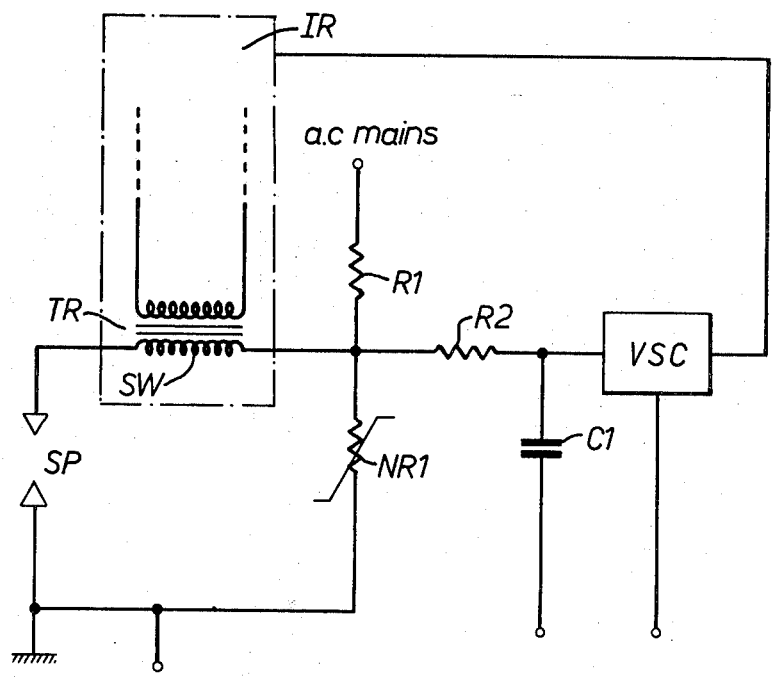
FIG. 1 is a circuit diagram of a single-burner flame detection arrrangement for use in a gas cooker provided with electric spark ignition and re-ignition facilities.

Referring to FIG. 1 of the drawings, the single-burner flame detection arrangement depicted comprises a non-linear resistance device NR 1 which is preferably a gas filled spark gap device of the form described in our co-pending application Ser. No. 20575/76 comprising a gas (e.g. argon) filled enclosure having cesium chloride coated electrodes of nickel or titanium for example and which is connected in series with a secondary winking SW of a spark generating transformer TR of an igniter/re-igniter circuit IR across a burner spark gap SP. The igniter/re-igniter circuit may be of any convenient form. The junction between the device NR1 and the secondary winding SW is connected to an a.c. mains supply through a resistor R1 which forms part of a filter network comprising resistors R1 and R2 of high resistance values, (e.g. 27 M ohms) and a capacitor C1 (e.g. 0.22 microFarads) which serve to filter out a.c. ripple. A voltage sensing means VSC detects the d.c. voltage input. The output from the voltage sensing means VSC may be directly connected to the igniter and re-igniter circuit referred to above.

For the ignition of gas at the burner, the igniter circuit IR will initially be operated, such as in response to the actuation of an appropriate gas tap on the cooker control panel, to produce high voltage pulses in the secondary winding SW of the transformer TR which produces sparking at the spark gap SP for the ignition of gas at the burner. For sparking to take place, the gas filled spark gap device NR1 breaks down and presents a low resistance when the spark voltage which is well above the mains voltage normally applied to it occurs, thereby allowing spark current to flow. At the same time the device NR1 by becoming low resistance limits the voltage across the filter network.

By considering the circuit diagram of FIG. 1, it will be appreciated that before the gas at the cooker burner is ignited, the spark gap SP and the device NR1 can be regarded as open-circuited so that the voltage at the input of the voltage sensing means VSC will be zero volts d.c. with a small a.c. ripple superimposed. In these circumstances an output from the voltage sensing means VSC may be utilised to cause the re-igniter circuit to be conditioned to provide voltage pulses to the transformer TR.

Figure 2:
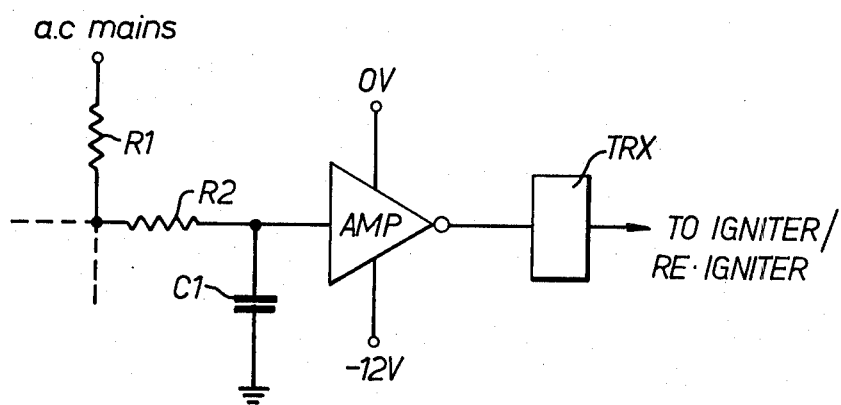
FIG. 2 shows a high impedance amplifier used as the voltage sensing means of FIG. 1.

Turning now to FIG. 2 of the drawings, this shows a high impedance amplifier AMP as the voltage sensing means VSC (FIG. 1) having the input thereof connected to the junction between resistor R2 and capacitor C1. The amplifier AMP is biased so that when there is zero d.c. volts input that is to say when there is no flame present at the burner, the amplifier provides an output (e.g.-12 volts) which operates a triggering device TRX to operate the igniter/re-igniter IR (FIG. 1). When flame is present at the burner then the d.c. voltage and the input to the amplifier AMP will be negative (e.g.-6 volts) in which event the output from the amplifier fails to operate the triggering device TRX for the operation of the igniter/re-igniter IR (FIG. 1).

In the case just referred to, where flame is present at the burner, the equivalent circuit of FIGS. 1 and 2 shown in FIG. 3 is applicable. The impedance of the secondary winding SW is negligible since the system is operated at mains frequency, (i.e. 50 cycles) and the inductance value of the winding SW is low, and since the voltage across the device NR1 (mains voltage) is insufficient to cause breakdown of the device, the device can be regarded as open-circuited. In the equivalent circuit of FIG. 3 the rectification flame diode across spark gap GP of FIG. 1 is represented by an ideal diode D1 and resistors Rf and Rr represent the forward resistance and reverse leakage, respectively, of the diode D1. The resistors R1 and R2 and the capacitors C1 are those shown in FIGS. 1 and 2.

$V_{in}$ represents the a.c. mains voltage and the waveform for this is shown at 7A. This voltage is asymmetrically attenuated by the resistor R1 and the diode network D1, Rf and Rr to provide the waveform shown at 7B. This negatively predominant waveform is filtered by the filter components R2 and C1 to provide a negative d.c. voltage, having a small percentage ripple as shown at 7C. This negative d.c. voltage is detected by the voltage sensing means VSC (FIG. 1) or AMP (FIG. 2) but any output therefrom fails to cause the re-ignition circuit to be operated. However, in the event of flame failure at the cooker burner, the voltage input to VSC or AMP will drop to zero d.c. volts as hereinbefore described whereupon a negative output from VSC or AMP (e.g.-12 volts) causes the re-igniter circuit to be operated so that high voltage pulses will be generated in the secondary winding SW for sparking at SP to re-ignite the gas burner.

In an alternative circuit arrangement shown in FIG. 4 and with reference to FIG. 8, the filter capacitor C1 (FIG. 1) is dispensed with in which case the mains a.c. voltage $V_{in}$ and zero d.c. volts applied to the input of the high impedance amplifier AMP when there is no flame present at the burner will cause the aplifier to produce a pulse output as shown at $V_o$ for the operation of the triggering device TRX. When flame is present at the burner the waveform $V_{in}$ will have low amplitude half cycles below the high impedance threshold of amplifier AMP so that the amplifier produces no output pulses for the operation of triggering device TRX.

Figure 5:
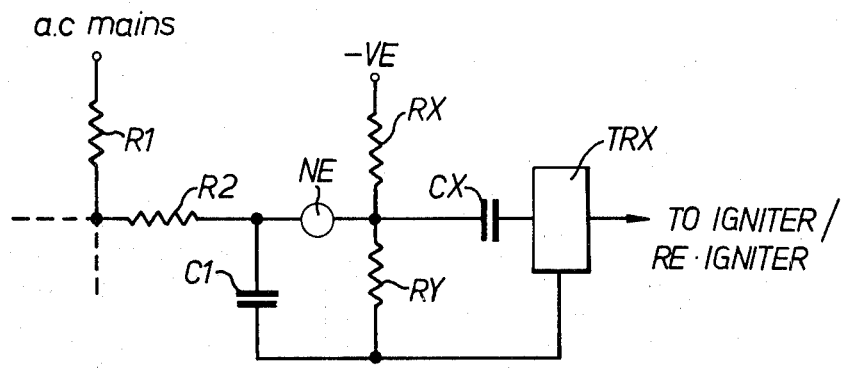
FIG. 5 shows a neon device used as the voltage sensing means of FIG. 1.

Referring now to FIG. 5 of the drawings the voltage sensing means comprises a neon device NE connected to the junction between the resistor R2 and capacitor C1. The output side of the device NE is connected to the junction between resistors RX and RY as well as through a capacitor CX to the input of triggering device TRX. Negative bias will be applied as shown to the neon device NE through resistor RX. In the case where no flame is present at the burner then the d.c. voltage at the input to the neon device NE will be zero volts so that the voltage across the neon will be sufficient to break it down and therby cause an input pulse to be delivered to the triggering device TRX through capacitor CX for the operation of the igniter/re-igniter circuit. When flame is present at the burner the d.c. voltage at the input to the neon device NE will be negative so that the voltage across the neon device is insufficient to cause it to break down for the operation of the triggering device TRX.

In an alternative arrangement to FIG. 5 the filter capacitor C1 is dispensed with so that under "no flame" conditions the mains a.c. voltage and zero d.c. volts are applied to the input of biased neon device NE and this will cause the device to break down on each positive half cycle of the mains a.c. but in the "flame" condition when the negative d.c. is superimposed on the a.c. the voltage across the neon device NE is insufficient to break down the neon and thereby initiate a gas re-ignition operation.

In an laternative embodiment of the invention the a.c. mains voltage is isolated from the flame detection arrangement by the interposition of an isolating transformer the secondary of which may be connected between the resistor R2 and the junction between the device NR1 and winding SW, the resistor R1 of FIGS. 1, 2, 4 and 5 being dispensed with. The primary of this isolating transformer will be connected to the mains supply.

Figure 6:
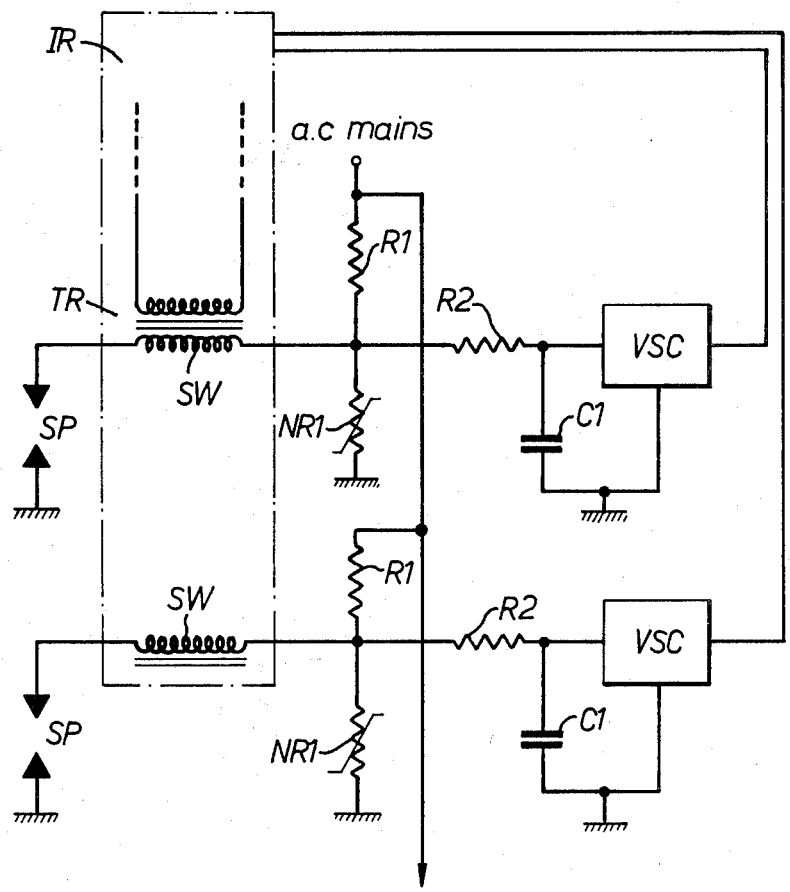
FIG. 6 is a circuit diagram of a flame detection arrangement similar to that shown in FIG. 1 but constructed for multi-burner operation.

In the FIG. 6 arrangement, it can be seen that a flame detection arrangement similar to that shown in FIG. 1 is provided in respect of each of a plurality of burners with the detection circuits being interconnected as shown. The igniter/re-igniter circuit IR is common to the multiburner arrangement with the spark generating transformer TR having one primary winding and a plurality of secondary windings SW.

Although the embodiments described with reference to the drawings relate to flame detection arrangements incorporated in a gas cooker, it will be understood that the invention is not limited to such application. For instance, the flame detection system could be applied to the control of a gas or oil-fired furnace or it may also be used in the detection of "hot gas" flowing along a pipeline by arranging that the air gap of FIG. 1 is located within the pipeline so that the "rectification effect" produced by the hot gas will enable the circuit to respond to give a warning signal output say when the flow of hot gas is interrupted.

What we claim is:

1. A circuit arrangement for detecting flame or hot gas in an air gap using the flame "rectification effect" comprising electrode means defining said air gap and connected on one side to an a.c. source and on the other side to a suitable potential for permitting current to flow in said air gap when flame or hot gas is present therein, non-linear resistance means connected across said air gap, voltage sensing means for detecting the voltage across the non-linear resistance means which is indicative of the presence or absence of flame or hot gas in said air gap, and filter means connected in the input path to the voltage sensing means so that any voltage appearing at the input to the voltage sensing means is a d.c. voltage with a small ripple superimposed thereon.

2. A circuit arrangement as claimed in claim 1, in which the voltage sensing means comprises a high impedance amplifier.

3. A circuit arrangement as claimed in claim 1, in which the voltage sensing means comprises a neon device.

4. A circuit arrangement as claimed in claim 1 for use in the detection of flame at the burner of a gas appliance, in which the secondary winding of a spark generating transformer is connected to the air gap so that when the voltage across the non-linear resistance means indicates the absence of flame in said air gap the voltage sensing means produces an output effective to trigger igniter/re-igniter means for pulsing said transformer and thereby cause sparking across said air gap for the ignition or re-ignition of gas.

5. A circuit arrangement as claimed in claim 4, in which the secondary winding of the spark-generating transformer is connected in series with the non-linear resistance means across the air gap.

6. A circuit arrangement as claimed in claim 1, in which isolation of the a.c. source from the air gap is effected by means of an isolating transformer the primary of which is connected to a.c. means and the secondary of which is connected in series with the voltage sensing means.

7. A plurality of circuit arrngements as claimed in claim 4, for use in a multi-burner gas cooker, in which the air gaps of said arrangements are individually associated with gas burners of said cooker in which the voltage sensing means of said arrangements are coupled to igniter/re-igniter means common to all said arrangements and in which the triggering of said igniter/re-igniter means by any one of said voltage sensing means produces pulsing of the spark generating transformer which has a single primary and a plurality of secondary windings connected respectively to the air gaps so that sparking is produced in all of said air gaps if flame absence or failure is detected at any of said gaps.

8. A circuit arrangement as claimed in claim 1, in which the non-linear resistance means is a gas-filled spark gap device.

* * * * *